United States Patent [19]
Herwig et al.

[11] Patent Number: 5,510,518
[45] Date of Patent: Apr. 23, 1996

[54] PROCESS FOR THE HYDROSULFINATION OF OLEFINS

[75] Inventors: Jürgen K. Herwig; Wilhelm Keim, both of Aachen, Germany

[73] Assignee: Hoechst Aktiengesellschaft, Frankfurt, Germany

[21] Appl. No.: 299,746

[22] Filed: Sep. 1, 1994

[30] Foreign Application Priority Data

Sep. 4, 1993 [DE] Germany .................. 43 29 932.6

[51] Int. Cl.⁶ .................................................. C07C 313/04
[52] U.S. Cl. ..................... 562/125; 562/120; 560/307; 568/31
[58] Field of Search ..................... 562/120, 125; 560/307; 568/31

[56] References Cited

FOREIGN PATENT DOCUMENTS 0220765  6/1987  European Pat. Off. .

OTHER PUBLICATIONS

Journal of Organic Chemistry, vol. 56, No. 19, Sep. 13, 1991, Furguson, et al., "Mercury–photosensitised suphinatio, hydrosulphination, and carbonylation of hydrocarbons: alkane and alkene conversion to sulphinic acid", pp. 5503–5510.

Journal of the Chemical Society, Chemical Communications, Keim et al., 1993, Palladium–catalyzed Hydrosulfination: Synthesis of Sulfonic Acids and S–Alkyl Alkanethiosulfonates from Alkenes, Sulphur Dioxide and Hydrogen.

Primary Examiner—Nicky Chan
Attorney, Agent, or Firm—Curtis, Morris & Safford

[57] ABSTRACT

Process for the preparation of olefins by using a palladium catalyst at a temperature above the ceiling temperature of the $SO_2$/olefin copolymer system, for the synthesis of sulfinic and sulfonic acid derivatives.

5 Claims, No Drawings

PROCESS FOR THE HYDROSULFINATION OF OLEFINS

Hydrosulfination, i.e. the addition of sulfur dioxide and hydrogen onto olefins, is a synthesis method which has hardly been paid attention to date.

Crabtree and colleagues thus describe the reaction of olefins, hydrogen and sulfur dioxide under intense UV irradiation by means of highly toxic mercury sensitizers. A product mixture which is oxidized with performic acid to give sulfonic acids is obtained (R. H. Crabtree, R. R. Ferguson, J. Org. Chem., 56, 1991, 5503).

No catalytic processes for the addition of $SO_2$ and $H_2$ onto olefins for simple synthesis of sulfinic acids, sulfonic acids and derivatives thereof are known.

The object: is therefore to develop a catalytic process for the hydrosulfination of olefins.

The invention relates to a process for the hydrosulfination of olefins, which comprises carrying out the hydrosulfination in the presence of palladium catalysts at a temperature above the ceiling temperature ($T_{Ceil}$) of the $SO_2$/olefin copolymer system (J. Polymer Sci. 26 (1957) 351) up to a temperature of 160° C.

Olefins which are suitable for the process according to the invention are $C_3$–$C_{18}$-alkenes, preferably $C_3$–$C_8$-alkenes, $C_3$–$C_6$-alkenyl-$C_6$–$C_{10}$-aryls and $C_5$–$C_8$-cycloalkenes. The alkenes can be branched or straight-chain, mono- or polyunsaturated and/or provided in the α-position with a group OR (R=$C_1$–$C_6$-alkyl, $C_6$–$C_{10}$-aryl) or with a group such as COOR, COR or CN, which leads to activation of the double bond. Alkenes having conjugated double bonds are not suitable.

Examples of mono- or polyunsaturated alkenes are propene, isobutene, n-hexene, dodecene, 1,9-decadiene and 1,5-hexadiene. Examples of cycloalkenes are cyclohexene and cyclopentene. Allylbenzene may be mentioned as an example of alkenylaryl. Examples of alkenes having activated double bonds are α,β-unsaturated carbonyl compounds and carboxylic acid esters, in particular methyl vinyl ketone and acrylic acid esters.

Particularly preferred olefins for the process according to the invention are propene, butene and isobutene.

$T_{Ceil}$ of the $SO_2$/olefin copolymer system is understood as meaning the temperature at which chain growth and chain disintegration are in equilibrium. No polymerization takes place above $T_{Ceil}$, i.e. monomeric olefin and $SO_2$ are present.

The hydrosulfination is preferably carried out at a temperature of 80° to 120° C.

Pd(II) salts having chelating ligands such as bis(di-$C_6$–$C_{10}$-arylphosphino)-$C_1$–$C_6$-alkyl and bis (di-$C_1$–$C_{12}$-alkylphosphino)-$C_1$–$C_4$-alkyl are preferably used as the catalyst. Bis(diphenylphosphino)-$C_2$–$C_4$-alkyl- and bis (di-$C_1$–$C_4$-alkylphosphino)-$C_2$–$C_4$-alkylpalladium (II) salts are particularly preferred. The amount of catalyst is 0.033 mmol/l–0.33 mol/l, preferably 0.333 mmol/l– 0.033 mol/l.

The molar ratio of olefin/$SO_2$ is 1:10–10:1, preferably 1:5–5:1, in particular 1:1.

The molar ratio of olefin/$H_2$ is 1:10–10:1, preferably 1:2–1:3.

For synthesis of a suitable catalyst, equimolar amounts of a Pd(II) salt, such as $PdCl_2$ or $PdBr_2$, and a ligand of the formula $R_2P(CH_2)_nPR_2$ (R=Me, Et, Pr, i-Pr, Ph, p-Tol, 2-MeOPh, Cy, t-Bu, n=1–6) are stirred in an inert solvent (for example DMSO) until all the Pd salt has reacted. The solvent is distilled off and the palladium complex formed is isolated in a quantitative yield. The palladium complex is suspended in a small mount of inert solvent and twice the molar amount of a salt of the formula MX (X=a non-coordinating anion, for example: $BF_4^-$, $B(C_6H_5)_4^-$, $B(C_6F_5)_4^-$, $PF_6^-$, $SbF_6^-$, M=Ag, Tl), dissolved in a weakly coordinating polar solvent (for example acetonitrile, dimethylformamide, dimethyl sulfoxide) is added. When the reaction is complete, the salt which has precipitated (MCl or MBr) is filtered off. The palladium catalyst can be isolated or employed directly as a solution.

The hydrosulfination reaction can be carried out in an autoclave with a stirring device, preferably in an inert gas atmosphere. The catalyst solution is added first. The $SO_2$ and the olefin are then introduced, and the hydrogen is then forced in. The sequence in which the olefin and $SO_2$ are introduced depends on the boiling point of the olefin used, i.e. olefins having a lower partial pressure than $SO_2$ are forced in before the $SO_2$.

Liquid olefins (for example 1-hexene) and other liquid additives are added directly after the catalyst solution. The $SO_2$ and the hydrogen are then forced in. Solid olefins and other solid additives are dissolved in a solvent and the solution is added to the autoclave. The gases are then forced in.

After cooling, the autoclaves are weighed and the final pressure is read off. The pressure is now released carefully and, after the gases dissolved in the solvent have been stirred out for a relatively long time, the autoclave is weighed again. The autoclave is undone and the reaction products are taken out. The solvent is then removed and the product which remains is analyzed.

The pure compounds are isolated by customary separation techniques (distillation, extraction, chromatography). Under the abovementioned conditions, thiosulfonic acid esters and sulfonic acids are formed in a molar ratio of 1:1 in the process according to the invention. Sulfinic acid and/or sulfinic acid derivatives are obtained by the process according to the invention if the hydrosulfination reaction is carried out in the presence of an alcohol and/or water, provided that the water is miscible with the actual solvent.

Suitable alcohols are $C_1$–$C_6$-alkanols, preferably methanol and ethanol. The molar ratio of catalysts to alcohol and/or water is 1:100–1:5000, preferably 1:500–1:1000. If an alkene having an activated double bond is employed as the olefin in the hydrosulfination reaction, the corresponding sulfinic acid is intermediately formed, and reacts further with excess olefin to give the corresponding sulfone.

If a 1-alkene and an alkene having an activated double bond are employed in the hydrosulfination reaction, the sulfinic acid formed from the 1-alkene reacts with the alkene having the activated double bond to give the corresponding γ-keto-sulfone.

The sulfinic and/or sulfonic acid derivatives obtainable by the process according to the invention are used as active compounds or active compound precursors for plant protection agents and pharmaceuticals. They can also be employed as intermediate products for reactive dyestuffs.

The synthesis of the catalysts used in the examples is described below:

Preparation of palladium [1,3-bis (diphenylphosphino)propane] (dichloride)

To prepare palladium [1,3-bis(diphenylphosphino)propane] (dichloride), 2.25 g of dppp (5.5 mmol) are added to 0.98 g of palladium chloride (5.5 mmol) in DMSO and the mixture is heated, while stirring, until the $PdCl_2$ has dissolved completely. On cooling, greenish palladium[1,3-bis-(diphenylphosphino)propane] (dichloride) precipitates out of the yellow-orange solution. The yield was 2.79 g= 86.4% of theory.

EXAMPLE 1

Thiosulfonic acid esters and sulfonic acids 0.01 mmol of (1,3-bis(diphenylphosphino)propane)palladium chloride is dissolved in 30 ml of $CH_2Cl_2$, and 0.02 mmol of $AgBF_4$, dissolved in 0.5 ml of acetonitrile, is added. The AgCl which has precipitated completely after stirring for 10 minutes is filtered off and the solution is transferred to a 150 ml Hastelloy autoclave with a magnetic stirrer. $SO_2$ is subsequently forced in up to a pressure of 3.5 bar, followed by propene up to a pressure of 8 bar and hydrogen up to a pressure of 25 bar. The autoclave is transferred to an oil bath preheated to 100° C. After 17 hours, the autoclave is first cooled to room temperature and then let down. The solvent is distilled off from the reaction mixture. 2 g of a mixture of isomeric propanethiosulfonic acid esters and sulfonic acids are obtained. The latter are obtained from the crude mixture by extraction with water and characterized by $^1H$- and $^{13}C$-NMR spectroscopy. The thiosulfonic acid esters are obtained in the pure form either by distillation (boiling point $_{1.3}$101° C.) or by column chromatography over silica gel columns (solvent:ethyl acetate/hexane 1:9) and are characterized by $^1H$- and $^{13}C$-NMR spectroscopy. The ratio of linear to branched chains can be determined by gas chromatography analysis in association with mass spectroscopy analysis. The isomer distribution for the propanethiosulfonic acid propyl esters is: n/n 77.4%, n/i+i/n 20.3%, i/i 2.3%.

EXAMPLE 2

Isolation of the sulfinic acids 0.1 mmol of (1,3-bis (diphenylphosphino)propane)palladium chloride is dissolved in 30 ml of $CH_2Cl_2$, and 0.2 mmol of $AgBF_4$, dissolved in 0.5 ml of acetonitrile, is added. The AgCl which has precipitated completely after stirring for 10 minutes is filtered off and the solution is transferred to a 150 ml Hastelloy autoclave with a magnetic stirrer. 2 g of methanol are introduced into the autoclave and $SO_2$ is subsequently forced in up to a pressure of 3.5 bar, followed by propene up to a pressure of 8 bar and hydrogen up to a pressure of 25 bar. The autoclave is transferred to an oil bath preheated to 100° C. After 17 hours, the autoclave is first cooled to room temperature and then let down. Methylene chloride and methanol are distilled off from the reaction mixture in vacuo at room temperature. 2.1 g of crude reaction mixture are obtained, of which 80% by weight is isomeric propanesulfinic acid and 20% by weight is isomeric propanesulfinic acid methyl esters ($^1H$-NMR). The sulfinic acids are obtained in the pure form by extraction with water. The mixture of sulfinic acids, like the propanesulfinic acid esters, comprises 85% by weight of linear and 15% by weight of branched products.

EXAMPLE 3

Isolation of the sulfones 0.1 mmol of (1,3-bis(diphenylphosphino)propane)palladium chloride is dissolved in 30 ml of $CH_2Cl_2$, and 0.2 mmol of $AgBF_4$, dissolved in 0.5 ml of acetonitrile, is added. The AgCl which has precipitated completely after stirring for 10 minutes is filtered off and the solution is transferred to a 150 ml Hastelloy autoclave with a magnetic stirrer. 5 ml of methyl vinyl ketone are introduced into the autoclave and $SO_2$ is subsequently forced in up to a pressure of 3.5 bar, followed by hydrogen up to a pressure of 25 bar. The autoclave is transferred to an oil bath preheated at 80° C. After 18 hours, the autoclave is first cooled to room temperature and then let down. The methylene chloride is distilled off from the reaction mixture. 0.8 g of bis(butan-3-one) sulfone is obtained. ($^1H$-NMR (ppm): 2.25 (s, 3H), 3.02 (t, 7 Hz, 2H), 3.30 (t, 7 Hz, 2H), $^{13}C$-NMR (ppm): 29.85, 35.32, 47.75, 203.86, IR($cm^{-1}$): 1713.7, 1239.8, 1136.4).

EXAMPLE 4

Isolation of the γ-ketosulfones 0.13 mmol of (1,3-bis(diphenylphosphino)propane)palladium chloride is dissolved in 30 ml of $CH_2Cl_2$, and 0.26 mmol of $AgBF_4$ is added. The AgCl which has precipitated completely after stirring for 10 minutes is filtered off and the solution is transferred to a 150 ml Hastelloy autoclave with a magnetic stirrer. 4 g of methylvinylketone are introduced into the autoclave, and $SO_2$ is subsequently forced in up to a pressure of 3.5 bar, propene is forced in up to a pressure of 8 bar and hydrogen is forced in up to a pressure of 25 bar. The autoclave is placed in an oil bath preheated at 80° C., and cooled to room temperature after 16.5 hours and let down. The methylene chloride and the acetonitrile are distilled off from the reaction product. 5.0 g of 4 -(propylsulfonyl)-2-butanone are obtained. The product is a mixture of 85% by weight of linear and 15% by weight of branched product.

We claim:

1. A process for the hydrosulfination of a $C_3$–$C_{18}$ olefin, which comprises carrying out the hydrosulfination in the presence of a palladium catalyst, $SO_2$ and hydrogen at a temperature above the ceiling temperature of the $SO_2$/olefin copolymer system up to a temperature of 160° C.

2. The process as claimed in claim 1, wherein the hydrosulfination is carried out in the presence of an alcohol and/or water in a molar ratio of 100:1– 5000:1 with respect to the catalyst.

3. The process as claimed in claim 1 wherein a Pd(II) salt having chelating ligands is used as the catalyst.

4. The process as claimed in claim 1, wherein a bisdiarylphosphinoalkanepalladium(II) salt is used as the catalyst.

5. The process as claimed in claim 1, wherein a bisdialkylphosphinoalkanepalladium(II) salt is used as the catalyst.

* * * * *